(12) United States Patent
Scarpine et al.

(10) Patent No.: US 10,532,185 B2
(45) Date of Patent: Jan. 14, 2020

(54) NAVIGABLE CATHETER DISTAL TIP CONFIGURATION

(71) Applicant: Covidien LP, Mansfield, MA (US)

(72) Inventors: Frank Scarpine, Brea, CA (US); Ricky Williams, Laguna Niguel, CA (US); Maria De Jesus Sanson, San Clemente, CA (US); Francis Bernard, Dana Point, CA (US)

(73) Assignee: Covidien LP, Mansfield, MA (US)

( * ) Notice: Subject to any disclaimer, the term of this patent is extended or adjusted under 35 U.S.C. 154(b) by 195 days.

(21) Appl. No.: 14/847,654

(22) Filed: Sep. 8, 2015

(65) Prior Publication Data

US 2017/0065793 A1    Mar. 9, 2017

(51) Int. Cl.
*A61M 25/00* (2006.01)
*A61B 17/22* (2006.01)
*A61B 8/12* (2006.01)

(52) U.S. Cl.
CPC .......... *A61M 25/0074* (2013.01); *A61B 8/12* (2013.01); *A61B 17/22* (2013.01); *A61B 2017/22079* (2013.01)

(58) Field of Classification Search
CPC ...... A61M 25/0074; A61M 2025/0046; A61M 25/09; A61M 25/0023; A61M 25/0067; A61M 2025/0081
See application file for complete search history.

(56) References Cited

U.S. PATENT DOCUMENTS

| 3,945,385 | A | | 3/1976 | Sackner |
| 4,961,731 | A | * | 10/1990 | Bodicky ........... A61M 25/0041 604/264 |
| 5,122,125 | A | | 6/1992 | Deuss |
| 5,738,666 | A | | 4/1998 | Watson et al. |
| 5,762,637 | A | * | 6/1998 | Berg ................... A61M 25/001 604/264 |
| 5,795,315 | A | * | 8/1998 | Traut ...................... A61F 5/055 128/DIG. 23 |
| 6,024,729 | A | | 2/2000 | Dehdashtian et al. |
| 6,866,655 | B2 | | 3/2005 | Hackett |
| 7,144,386 | B2 | | 12/2006 | Korkor et al. |
| 7,547,304 | B2 | | 6/2009 | Johnson |
| 8,343,091 | B2 | | 1/2013 | Schweikert |

(Continued)

FOREIGN PATENT DOCUMENTS

WO        9505862  A1    3/1995

*Primary Examiner* — Nathan R Price
*Assistant Examiner* — Tasnim Mehjabin Ahmed
(74) *Attorney, Agent, or Firm* — Shumaker & Sieffert, P.A.

(57) ABSTRACT

In some examples, a catheter includes an elongated body extending between a proximal end and a distal end, and defining an inner lumen, an outer body wall having a wall cross-sectional diameter, and a distal aperture at the distal end. A distal portion of the elongated body including a taper section that tapers from the outer body wall of the distal portion to the distal aperture, with the distal portion defining a plurality of slits open to the distal aperture. The distal aperture has an aperture diameter greater than zero and less than the wall cross-sectional diameter. The distal portion defining the plurality of slits is configured to substantially center the distal end around a guide member when the guide member is introduced in the inner lumen and extends through the distal aperture.

25 Claims, 7 Drawing Sheets

(56) References Cited

U.S. PATENT DOCUMENTS

| | | | |
|---|---|---|---|
| 2005/0033311 A1* | 2/2005 | Guldfeldt | A61M 25/04 606/108 |
| 2007/0244440 A1* | 10/2007 | Pal | A61M 25/0074 604/164.13 |
| 2011/0144661 A1* | 6/2011 | Houser | A61B 17/0057 606/142 |
| 2011/0313404 A1* | 12/2011 | Amos | A61F 2/95 604/544 |
| 2013/0053825 A1 | 2/2013 | Moulton et al. | |
| 2014/0074144 A1 | 3/2014 | Shrivastava et al. | |
| 2014/0128844 A1 | 5/2014 | Kornowski et al. | |

* cited by examiner

NAVIGABLE CATHETER DISTAL TIP CONFIGURATION

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, this disclosure describes example catheters that include an elongated body having a distal portion defining a distal aperture at a distal end. The distal portion tapers from an outside body diameter of the elongated body to a diameter of the distal aperture. The distal portion may include a plurality of slits opening to the distal aperture. The taper of the distal portion along with the plurality of slits may help center the distal end of the catheter about a guide member and reduce the occurrence of ledge effects as the catheter is advanced through a vasculature of a patient, while still maintaining a relatively large effective distal opening. This disclosure also describes example methods of forming catheters and methods of using catheters.

Clause 1: In one example, a catheter including an elongated body extending between a proximal end and a distal end, and defining an inner lumen, an outer body wall having a wall cross-sectional diameter, and a distal aperture at the distal end, a distal portion of the elongated body comprises a taper section that tapers from the outer body wall of the distal portion to the distal aperture, the distal portion defining a plurality of slits open to the distal aperture, the distal aperture has an aperture diameter greater than zero and less than the wall cross-sectional diameter, and the distal portion defining the plurality of slits is configured to substantially center the distal end around a guide member when the guide member is introduced in the inner lumen and extends through the distal aperture.

Clause 2: In some examples of the catheter of clause 1, the plurality of slits extend radially outward from the distal aperture.

Clause 3: In some examples of the catheter of clause 1, the plurality of slits spiral radially outward from the distal aperture.

Clause 4: In some examples of the catheter of clause 1, the aperture diameter of the distal aperture is about 0.2 mm to about 0.8 mm.

Clause 5: In some examples of the catheter of clause 4, the aperture diameter of the distal aperture is about 0.36 mm.

Clause 6: In some examples of the catheter of clause 1, the taper section includes a lubricious outer surface.

Clause 7: In some examples of the catheter of clause 1, the distal portion is thermally bonded to the elongated body.

Clause 8: In some examples of the catheter of clause 1, the taper section has a total length of less than about 10 mm.

Clause 9: In some examples of the catheter of clause 1, the outer body wall lacks any openings therein.

Clause 10: In some examples of the catheter of clause 9, the outer body wall is a sidewall of the elongated body.

Clause 11: In some examples of the catheter of clause 1, the taper section includes a plurality of tip flaps defined by the plurality of slits, the plurality of tip flaps are configured to retract proximally along the distal portion to change the size of the distal aperture.

Clause 12: In some examples of the catheter of clause 1, the distal aperture is positioned in a distalmost tip of the catheter.

Clause 13: In one example, an assembly including a catheter including an elongated body extending between a proximal end and a distal end, and defining an inner lumen, an outer body wall having a wall cross-sectional diameter, and a distal aperture at the distal end, wherein a distal portion of the elongated body comprises a taper section that tapers from the outer body wall to the distal aperture, the distal portion defining a plurality of slits open to the distal aperture, the distal aperture has an aperture diameter greater than zero and less than the wall cross-sectional diameter, and a guide member disposed within the inner lumen of the catheter and extending through the distal aperture of the catheter, where the distal end of the elongated body engages with the guide member to substantially center the distal end of the of the elongated body relative to the guide member.

Clause 14: In some examples of the assembly of clause 13, the plurality of slits extend radially outward from the distal aperture.

Clause 15: In some examples of the assembly of clause 13, the plurality of slits spiral radially outward from the distal aperture.

Clause 16: In some examples of the assembly of clause 13, the aperture diameter of the distal aperture is about 0.2 mm to about 0.8 mm.

Clause 17: In some examples of the assembly of clause 13, the aperture diameter of the distal aperture is about 0.36 mm.

Clause 18: In some examples of the assembly of clause 13, the taper section of the catheter includes a lubricious outer surface.

Clause 19: In some examples of the assembly of clause 13, the taper section has a total length of less than about 10 mm.

Clause 20: In some examples of the assembly of clause 13, the outer body wall lacks any openings therein.

Clause 21: In some examples of the assembly of clause 20, the outer body wall is a sidewall of the elongated body.

Clause 22: In some examples of the assembly of clause 13, the taper section includes a plurality of tip flaps defined by the plurality of slits, the plurality of tip flaps are configured to retract proximally along the distal portion to change the size of the distal aperture.

Clause 23: In some examples of the assembly of clause 13, the distal aperture is positioned in a distalmost tip of the catheter.

Clause 24: In some examples of the assembly of clause 13, the guide member comprises a guidewire.

Clause 25: In some examples of the assembly of clause 13, the catheter comprises a first catheter, and wherein the guide member comprises a second catheter.

Clause 26: In one example, a method including inserting a guide member into a vasculature of a patient. The method including introducing a catheter over the guide member, the catheter includes an elongated body extending between a proximal end and a distal end, and defining an inner lumen for receiving the guide member, an outer body wall having a wall cross-sectional diameter, and a distal aperture at the distal end, a distal portion of the elongated body include a taper section that tapers from the outer body wall to the distal aperture, the distal aperture has an aperture diameter greater than zero and less than the wall cross-sectional diameter. The method including substantially centering the distal end of the catheter around the guide member via the taper section. The method including advancing the distal portion of the catheter along the guide member to a treatment site in the vasculature of the patient. The method including where the distal portion of the elongated body defines a plurality of slits open to the distal aperture, the distal portion being configured to substantially center the distal end around the guide member when the guide member is introduced in the inner lumen and extends through the distal aperture.

Clause 27: In some examples of the method of clause 26, the aperture diameter of the distal aperture is about equal to a cross-sectional diameter of the guide member.

Clause 28: In some examples of the method of clause 26, the guide member has a cross-sectional diameter of about 0.2 mm to about 0.8 mm, and the wall cross-sectional diameter is about 1 mm to about 2.67 mm.

Clause 29: In some examples of the method of clause 26, advancing the distal portion of the catheter along the guide member includes advancing the catheter directly over the guide member.

Clause 30: In some examples of the method of clause 26, advancing the distal portion of the catheter along the guide member to the treatment site in the vasculature of the patient further includes advancing the distal portion of the catheter along a curved portion of the guide member in a curved vasculature, and inhibiting the distal portion from damaging an inner wall of the curved vasculature by maintaining the distal end substantially centered around the guide member.

Clause 31: In some examples of the method of clause 26, advancing the distal portion of the catheter along the guide member to the treatment site in the vasculature of the patient further includes advancing the distal portion of the catheter along a curved portion of the guide member in a curved vasculature, and inhibiting the distal portion from damaging an inner wall of the blood vessel by virtue of the taper section.

Clause 32: In some examples of the method of clause 26, further including removing a thrombosis from the vasculature of the patient through the distal aperture of the catheter.

Clause 33: In some examples of the method of clause 26, the taper section includes a plurality of tip flaps defined by the plurality of slits, the method further including retracting the plurality of tip proximally along the distal portion to change the size of the distal aperture.

Clause 34: In one example, a method including forming a catheter including an elongated body extending between a proximal end and a distal end, and defining an inner lumen, an outer body wall having a wall cross-sectional diameter, and a distal aperture at the distal end, a distal portion of the elongated body includes a taper section that tapers from the outer body wall to the distal aperture, and the distal aperture has an aperture diameter greater than zero and less than the wall cross-sectional diameter. The method including forming a plurality of slits in the distal portion of the elongated body, the plurality of slits being open to the distal aperture, the distal portion defining the plurality of slits is configured to substantially center the distal end around a guide member when the guide member is introduced in the inner lumen and extends through the distal aperture.

Clause 35: In some examples of the method of clause 34, forming the plurality of slits at the distal portion of the catheter includes cutting the plurality of slits into the distal portion of the catheter, the plurality of slits spiral radially outward from the distal aperture of the catheter.

Clause 36: In some examples of the method of clause 34, forming the plurality of slits includes cutting the plurality of slits in the distal portion of the catheter, the plurality of slits extend radially outward from the distal aperture.

Clause 37: In some examples of the method of clause 34, the taper section includes a plurality of tip flaps defined by the plurality of slits, the plurality of tip flaps are configured to retract proximally along the distal portion to change the size of the distal aperture.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

A medical catheter ("catheter") described herein includes a relatively flexible elongated body (e.g., the body of the catheter) that is configured to be navigated through vasculature of a patient, e.g., tortuous vasculature in a brain of the patient. The elongated body includes a distal potion that tapers (e.g., convexly curves) from the diameter of the outer body wall (e.g., a sidewall of the elongated body) to a distal aperture at the distal end of the elongated body. The taper of the distal portion helps center the distal end of the catheter around a guide member (e.g. a guidewire, an inner catheter, or both) as the catheter is advanced through the vasculature of a patient. The distal portion also includes a plurality of slits that open to a distal aperture positioned at the distal end of the elongated body. The plurality of slits provide a relatively small distal opening to engage with the guide member and help center the distal end of the elongated body about the guide member as the elongated body is advanced through the vasculature, while also providing a relatively large effective distal opening (e.g., when the distal tip is expanded outward or retracted inward) that may be used for aspirating, delivering a treatment device, or the like. The elongated body may be configured with a relatively large inner lumen (also referred to as a working channel in some examples), through which tissue sites distal to the catheter may be accessed, for example, to deliver a medical device or therapeutic agent, to remove a thrombus or other target from the patient's body, or any combination thereof. In some examples, the relatively large inner lumen of the catheter may provide for more efficient and/or more effective aspiration of thrombosis from the vasculature compared to catheter bodies having smaller inner lumens, e.g., due to a larger aspiration force that can be applied to the catheter, due to the larger catheter inner lumen for receiving the thrombosis, or both. Additionally or alternatively, in some examples, the relatively large inner lumen of the catheter may accommodate a larger range of medical devices and a larger range of fluid volumes. Thus, the catheter body defining a relatively large inner diameter may be used with a larger range of medical procedures.

The elongated body may be formed of relatively rigid materials to permit the catheter body to be advanced through a vasculature of a patient without buckling or undesirable bending (e.g., kinking) of the catheter body, yet maintain a degree of flexibility that allows the substantially conform to the curvature of the vasculature. In addition, in some examples, the catheter body has a columnar strength and flexibility that allow at least a distal portion of the catheter body to be navigated from a femoral artery, through the aorta of the patient, and into the intracranial vasculature system of the patient, e.g., to reach a relatively distal treatment site, including the middle cerebral artery (MCA), the Circle of Willis, and tissue sites more distal than the MCA and the Circle of Willis. The MCA and, consequently, vasculature distal to the MCA may be relatively difficult to access due to the carotid siphon or vertebral artery anatomy that must be traversed to reach such locations.

In some cases, a clinician may steer a catheter through the vasculature of a patient by rotating the catheter. A distal portion of the elongated body leads a proximal portion of the catheter through the vasculature, and may, therefore, be introduced in the patient while the proximal portion is external to the patient. The clinician may apply torque to the proximal portion of the catheter (or at least a portion of the elongated body that is more proximal than the distal portion implanted in the patient) in order to rotate the distal portion of the catheter. Thus, some examples of a catheter described herein include an elongated body that is configured to transmit torque applied to a relatively proximal portion to a relatively distal portion. The elongated body may be relatively resistant to kinking upon rotation of the catheter body from the relatively proximal portion of the catheter body. For example, the catheter body may include a structural support member (e.g., a helical coil member or a braided member), which is configured to help distribute the torsional forces along the catheter body.

In some examples, the catheter may be an aspiration catheter in which the inner lumen defined by the catheter body is used to remove thrombus from a vasculature. In such examples, a vacuum may be applied to a proximal end of the elongated body to suction and draw a thrombus into the inner lumen of the catheter without the elongated body collapsing under the vacuum pressure. An aspiration catheter may be used in a medical procedure to treat an ischemic insult, which may occur due to occlusion of a blood vessel that deprives brain tissue of oxygen-carrying blood.

The catheters described by this disclosure may be advanced to a treatment location within vasculature of the patient in cooperation with a guide member (e.g., a guidewire, an inner catheter, or both), which may aid in the navigation (e.g., steering and manipulation) of the catheter through the vasculature. For example, an inner lumen of the catheter body may be configured to receive the guide member such that the catheter body may be guided through vasculature over the guide member. As described in further detail below, the distal portion of the elongated body of the catheter may taper inward from the outer diameter of the elongated body to a distal aperture at the distal end. The distal portion may define a plurality of slits opening from the distal aperture, such that the slits in conjunction with the taper of the distal portion substantially center (e.g., centers or nearly centers) the distal end of the catheter around the guide member as the catheter is advanced through the vasculature of the patient to the treatment cite. While examples described below primarily refer to a guide member that is a guidewire, in other examples, the guide member may be another catheter, a combination of a guidewire and catheter, or other suitable elongate member.

In some examples, the self-centering aspect of the distal portion of the catheter may help prevent or reduce the occurrence of a catheter ledge-effect. A ledge-effect may otherwise cause the distal end of the catheter to catch on or abrade certain anatomical features as it is advanced through vasculature of the patient, which may adversely affect the navigability and atraumaticity of the catheter. By centering the distal end of the catheter around the guide member, the catheter may be better positioned within the vasculature of the patient, thereby improving the ease with which a clinician may guide the catheter to a relatively distal vasculature treatment site through a series of tight turns in the vasculature. Although primarily described as being used to reach relatively distal vasculature sites, the catheters described herein may be used readily for other target tissue sites within the body of a patient.

Figure 1:
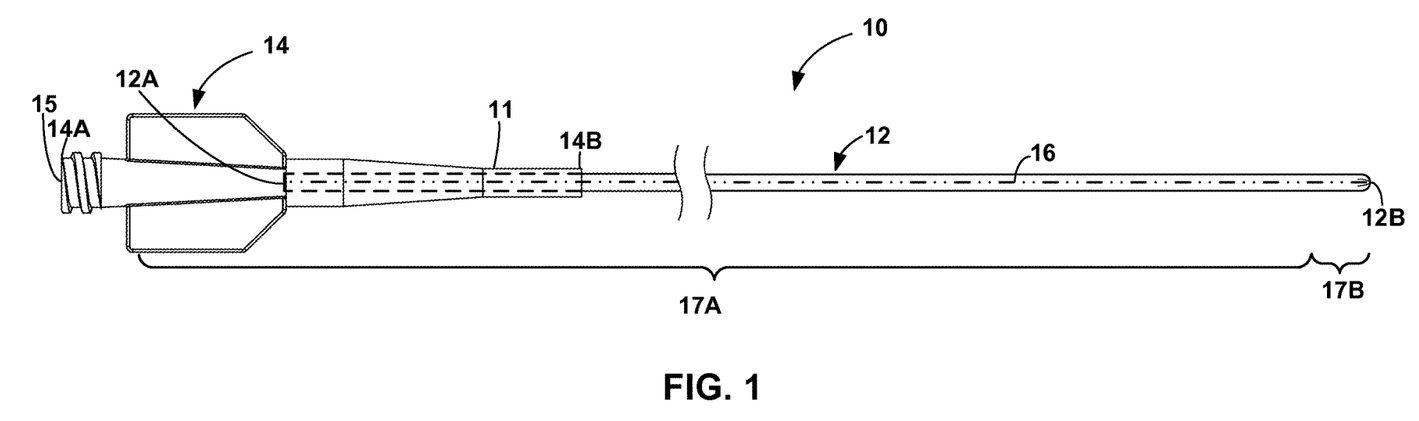
FIG. 1 is a conceptual side view of an example catheter, which includes an elongated body and a hub.

FIG. 1 is a conceptual side view of an example catheter 10, which includes elongated body 12 of catheter 10 and a hub 14 positioned at a proximal end 12A of elongated body 12. Elongated body 12 may extend from proximal end 12A to distal end 12B, and defines a proximal portion 17A and distal portion 17B. Elongated body 12 may define at least one inner lumen 26 (shown in FIG. 3) that extends the length of elongated body. In the example shown in FIG. 1, proximal end 12A of catheter 12 is received within hub 14 and can be mechanically connected to hub 14 via an adhesive, welding, or another suitable technique or combination of techniques. Opening 15 defined by hub 14 and located at proximal end 14A of hub 14 is aligned with the inner lumen 26 (shown in FIG. 3) of elongated body 12, such that the inner lumen 26 of elongated body 12 may be accessed via opening 15. In some examples, catheter 10 may include a strain relief body 11, which may be a part of hub 14 or may be separate from hub 14.

In other examples, the proximal end of catheter 10 can include another structure in addition or instead of hub 14. In some examples, catheter hub 14 may define an opening through which an inner lumen 26 (shown in FIG. 3) of elongated body 12 may be accessed and, in some examples, closed. For example, catheter hub 14 may include one or more luers or other mechanisms for establishing connections between catheter 10 and other devices.

As described in further detail below, elongated body 12 may be used to access relatively distal vasculature locations in a patient, such as the MCA in a brain of a patient. The MCA, as well as other vasculature in the brain or other relatively distal tissue sites (e.g., relative to the vasculature access point), may be relatively difficult to reach with a catheter, due at least in part to the tortuous pathway (e.g., comprising relatively sharp twists and/or turns) through the vasculature to reach these tissue sites. Elongated body 12 is structurally configured to be relatively flexible, pushable, and relatively kink- and buckle-resistant, so that it may resist buckling when a pushing force is applied to a relatively proximal portion of the catheter to advance the catheter body distally through vasculature, and so that it may resist kinking when traversing around a tight turn in the vasculature. Unwanted kinking and/or buckling of elongated body 12 may hinder a clinician's efforts to push the catheter body distally, e.g., past a turn.

Elongated body 12 has a suitable length for accessing a target tissue site within the patient from a vasculature access point. The length may be measured along longitudinal axis 16 of elongated body 12. In some examples the working length of elongated body 12 may be measured from hub distal end 14B of hub 14 (marked by the distal end of optional strain relief body 11) to distal end 12B of distal portion 17B. The working length of catheter 10 may depend on the location of the target tissue and/or the medical procedure for which catheter 10 is used. For example, if catheter 10 is a distal access catheter used to access vasculature in a brain of a patient from a femoral artery access point at the groin of the patient, catheter 10 may have a working length of about 129 centimeters (cm) to about 135 cm, such as about 132 cm, although other lengths may be used. In other examples, or for other applications, the working length of elongated body 12 may have different lengths.

In some examples, elongated body 12 may define an outer diameter gradient along its working length (different than the taper of distal portion 17B described below). The outer diameter gradient may assist with the pushability and/or flexibility of elongated body 12. In some examples, the outer diameter gradient may define a smooth transition from outer diameter of proximal end 12A to the outer diameter of distal portion 17B. In other examples, proximal portion 17A may progressively change in outer diameter, e.g., it may define discrete step-downs in outer diameter to define the outer diameter gradient. The size of the discrete step-downs in diameter may be selected to reduce the number of edges that may potentially catch on anatomical features within the vasculature as elongated body 12 is advanced through vasculature.

In some examples, at least a part (e.g., only part of the length or the entire length) of proximal portion 17A may define a constant outer diameter. For example, the constant outer diameter in proximal portion 17A may be substantially equal (e.g., equal or nearly equal) to the outer diameter of distal portion 17B (e.g., OD of FIG. 2). A larger outer diameter of proximal portion 17A may provide better proximal support for elongated body 12, which may help increase the pushability of elongated body 12. In contrast, in some examples in which elongated body 12 of catheter 10 has a constant diameter along the length of elongated body 12 (with the exception of taper section 20), the constant diameter may be selected to facilitate distal flexibility of the elongated body 12, and, as a result, may be configured with less proximal support.

Catheter 10 having a smaller outer diameter may be easier to navigate through tortuous vasculature. Thus, by reducing the outer diameter of elongated body 12 at distal portion 17B, which leads elongated body 12 through vasculature, elongated body 12 may better traverse through tortuous vasculature with still maintaining a relatively high level of proximal pushability. In some cases, proximal portion 17A may not be introduced into low profile or tortuous arteries, such that the cross-sectional size of proximal portion 17A may be increased in favor of proximal support without adversely affecting the ability of elongated body 12 to reach relatively distal tissue sites.

In some examples, the outer diameter of elongated body 12 may taper from about 6 French (e.g., 6 French or nearly 6 French) at proximal end 12A to about 5 French (e.g., 5 French or nearly 5 French) at the distal portion 17B (e.g., proximal to taper section 20). In other examples, the outer diameter of elongated body 12 may taper from about 4 French (e.g., 4 French or nearly 4 French) at proximal end 12A to about 5 French (e.g., 3 French or nearly 3 French) at the distal portion 17B. In other examples, the outer diameter of elongated body 12 may remain substantially constant (e.g., constant or nearly constant) in the range of about 3 French and about 6 French (with the exception of distal portion 17B). In some examples, the outer diameter of elongated body 12 may be larger than 6 French, for example 8 French. The measurement term French, abbreviated Fr or F, is three times the diameter of a device as measured in millimeters (mm). Thus, a 8 French diameter is about 2.67 mm, a 6 French diameter is about 2 mm, a 5 French diameter is about 1.67 mm, a 4 French diameter is about 1.33 mm, and a 3 French diameter is about 1 mm. In some examples, the outer diameter of elongated body 12 may be between about 1 mm to about 2.67 mm.

In some examples, elongated body 12 may be formed from two or more discrete and separate longitudinally extending segments that are mechanically connected to each other, e.g., at axial butt joints. In other examples elongated body 12 may be substantially continuous along a length of elongated body 12.

In some examples, at least a portion of an outer surface of elongated body 12 includes one or more coatings, such as, but not limited to, an anti-thrombogenic coating, which may help reduce the formation of thrombi in vitro, an anti-microbial coating, and/or a lubricating coating. In some examples, the entire working length of elongated body 12 (from distal portion 14B of hub 14 to distal end 12B) is coated with the hydrophilic coating. In other examples, only a portion of the working length of elongated body 12 coated with the hydrophilic coating. This may provide a length of elongated body 12 distal to distal end 14B of hub 14 with which the clinician may grip elongated body 12, e.g., to rotate elongated body 12 or push elongated body 12 through vasculature.

In some examples, elongated body 12 may be include a structural support member, e.g., a coil member or a braided member, configured to increase the structural integrity of elongated body 12 while allowing elongated body 12 to remain relatively flexible. For example, the support layer may be configured to help elongated body 12 substantially maintain its cross-sectional shape substantially throughout proximal and distal portions 17A and 17B or at least help prevent elongated body 12 from buckling or kinking as it is navigated through tortuous anatomy. As a result, a clinician may apply pushing forces, rotational forces, or both, to proximal portion 17A of elongated body 12, and such forces may cause distal portion 17B of elongated body 12 to advance distally, rotate, or both, respectively. Materials that may be used to for the support layer include, for example, metals, such as stainless steel or a nickel-titanium alloy (e.g., Nitinol).

In some examples, the stiffness along elongated body 12 may vary along longitudinal axis 16. For example, the proximal end 12A of proximal section 17A may have a durometer greater than or equal to about 72D that transitions to a durometer greater than about 24D along longitudinal axis 16 towards distal end 12B. The hardness of elongated body 12 (or portions thereof) may be selected to obtain more or less flexibility, torqueability, and pushability for all or part of elongated body 12.

In some examples, elongated body 12 may include radiopaque marker (not shown), which may be attached to distal portion 17B. In some examples, the radiopaque marker may be on the outer surface, partially embedded, or along the inner surface of elongated body 12. The radiopaque marker may be formed from any suitable material, and may be in the form of a continuous ring, a discontinuous ring, or multiple segments that extend around, in, or within elongated body 12. The radiopaque marker may be positioned to indicate the location of certain portions of elongated body 12 (e.g., distal end 12B) and positioned accordingly.

Figure 2:
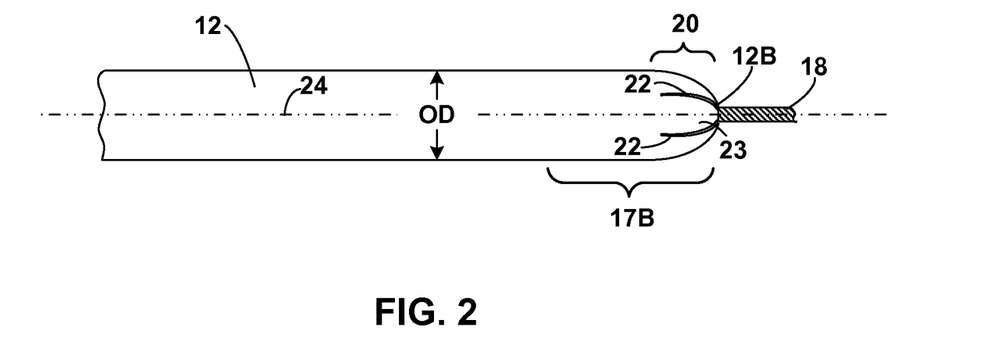
FIG. 2 is a conceptual side view of part of an example elongated body of the catheter of FIG. 1.
Figure 3:
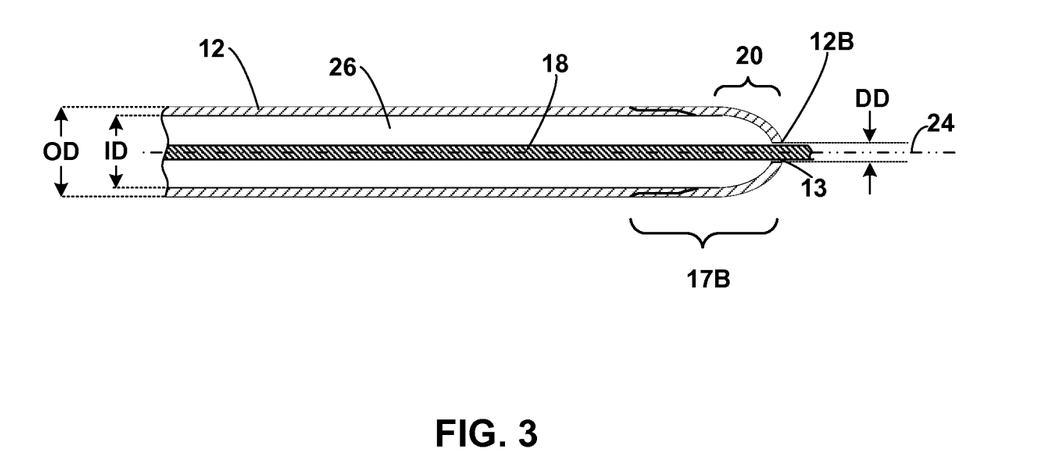
FIG. 3 is a conceptual cross-sectional view of part of an example assembly that includes the elongated body of the catheter of FIG. 1 and a guide member.

FIGS. 2 and 3 show a conceptual side view and cross-sectional view respectively of a part of elongated body 12 including distal portion 17B. Distal portion 17B can include a taper section 20, where the elongated body 12 tapers from the outer body wall (e.g. outer diameter OD of a sidewall of elongated body 12) to a distal aperture 13 at distal end 12B. Distal portion 17B may also define a plurality of slits 22 that open to distal aperture 13, such that plurality of slits 22 define tip flaps 23 along taper section 20 configured to center distal end 12B of catheter 10 around a guide member 18. Plurality of slits 22 together with distal aperture 13 also may be configured to allow taper section 20 to expand (e.g., via straightening of tip flaps 23 to or toward an orientation parallel to longitudinal axis 16 of elongated body 12) to allow a clinician to advance, for example, a treatment device (not shown) through the inner lumen 26 and past the distal end 12B of elongated member 12 into the vasculature of a patient.

In some examples, catheter 10 may be a part of an assembly that includes, e.g., a guide member 18 (e.g., a guidewire), which may be used to guide elongated body 12 to a target tissue site within the vasculature of a patient as described in more detail below.

In some examples, the diameter of inner lumen 26 (e.g., ID) of elongated body 12, also referred to herein as an inner diameter of elongated body 12, may be substantially continuous (e.g., continuous or nearly continuous) from proximal end 12A to the proximal end of taper section 20. In other examples, a portion of inner diameter of elongated body 12 may include an inner diameter gradient (different than the taper of taper section 20 described below) along the length of elongated body 12 (with the exception of taper section 20). For example, an inner diameter of elongated body 12 may define a first inner diameter of about 1.74 mm (about 0.0685 inches) at proximal end 12A and decrease to a second inner diameter of about 1.54 mm (about 0.0605 inches) at or near the proximal end of taper section 20. In some examples, the inner diameter gradient of inner lumen 26 may be continuous (e.g., gradually decrease or narrow), discontinuous (e.g., step-wise decreasing or narrowing), or a combination of both. In some examples, the diameter of inner lumen 26 may depend on the intended application of catheter 10. For example, the diameter of inner lumen 26 may be sized to receive a medical device (e.g., a thrombectomy device, an embolic protection device, a stent, or another device), a liquid embolic composition, a therapeutic agent, or the like.

In some examples, elongated body 12 may be relatively thin-walled, such that it defines a relatively large inner diameter of inner lumen 26 (e.g., ID shown in FIG. 3) for a given outer body diameter (e.g., OD shown in FIG. 3), which may further contribute to the flexibility and kink-resistance of elongated body 12. The wall thickness of elongated body 12 may be half the difference between the outer diameter of elongated body 12 (e.g., OD shown in FIG. 3) and the inner diameter of elongated body 12, as defined by inner lumen 26 (e.g., ID shown in FIG. 3). A larger inner diameter to outer diameter ratio may be useful for aspiration, target (e.g., thrombosis) capture, as well as maneuvering devices within inner lumen 26, such that the increasing the inner diameter to outer diameter ratio may be desirable.

In some examples, inner lumen 26 may be defined by an inner liner, which may be a tubular body that extends from proximal end 12A of elongated body to distal end 12B. At least the inner surface of the inner liner may be lubricious in some examples in order to facilitate the introduction and passage of a device, a therapeutic agent, or the like, through inner lumen 26. Example materials for the inner liner may include, but are not limited to, polytetrafluoroethylene (PTFE), fluoropolymer, perfluoroalkyoxy alkane (PFA), fluorinated ethylene propylene (FEP), or any combination thereof.

In some examples, inner lumen 26 and distal aperture 13 may be configured to receive a guide member 18 that may facilitate navigation of distal portion 17B of elongated body 12 to a treatment site within the vasculature of a patient. In such examples, guide member 18 may be initially inserted in a vasculature of a patient and guided by the clinician to treatment site within the body of a patient. A proximal end of guide member 18 (e.g., an end of guide member 18 extending outside of the body of the patient) may then be inserted into inner lumen 26 through distal aperture 13 of elongated body 12. The clinician may then advance distal portion 17B of the catheter along guide member 18 to the treatment site.

In some examples, distal aperture 13 may define a diameter (DD) greater than zero but less than the diameter of outer body wall (e.g. outer diameter (OD) of elongated body 12) when plurality of slits 22 are substantially closed (e.g., when taper section 20 is in a relaxed or non-expanded state). In some examples, distal aperture 13 may be defined by a diameter (DD) substantially the same (e.g., the same or nearly the same) or less than the diameter of guide member 18. In such examples, the diameter of distal aperture 13 (DD) may allow distal end 12B of elongated body 12 to remain substantially centered (e.g., centered or nearly centered) about guide member 18 while allowing the clinician to advance elongated body 12 along guide member 18 without significant resistance. For example, as shown in FIG. 2, longitudinal axis 24 defines the center axis of elongated body 12 and distal aperture 13 as well as the center axis of guide member 18. In some examples where the diameter of distal aperture 13 (DD) is substantially the same or less than the diameter of guide member 18, distal end 12B of elongated body 12 may contact guide member 18 (e.g., contact about the area defined by distal aperture 13), thereby substantially centering distal end 12B of elongated body 12 so that the center axis 24 of the distal aperture 13 and guide member 18 remain substantially aligned (e.g., aligned or nearly aligned). In such examples, even though guide member 18 may contact portions of inner lumen 26 (e.g., contact inner lumen 26 around proximal portion 17A), distal end 12B remains substantially centered about guide member 18. In some examples, diameter of distal aperture 13 (DD) may be about 0.2 mm to about 0.8 mm (about 0.008 inches to about 0.030 inches), e.g. about the diameter of a guidewire. In some examples, diameter of distal aperture 13 (DD) may be about 0.36 mm (about 0.014 inches).

Figure 4:
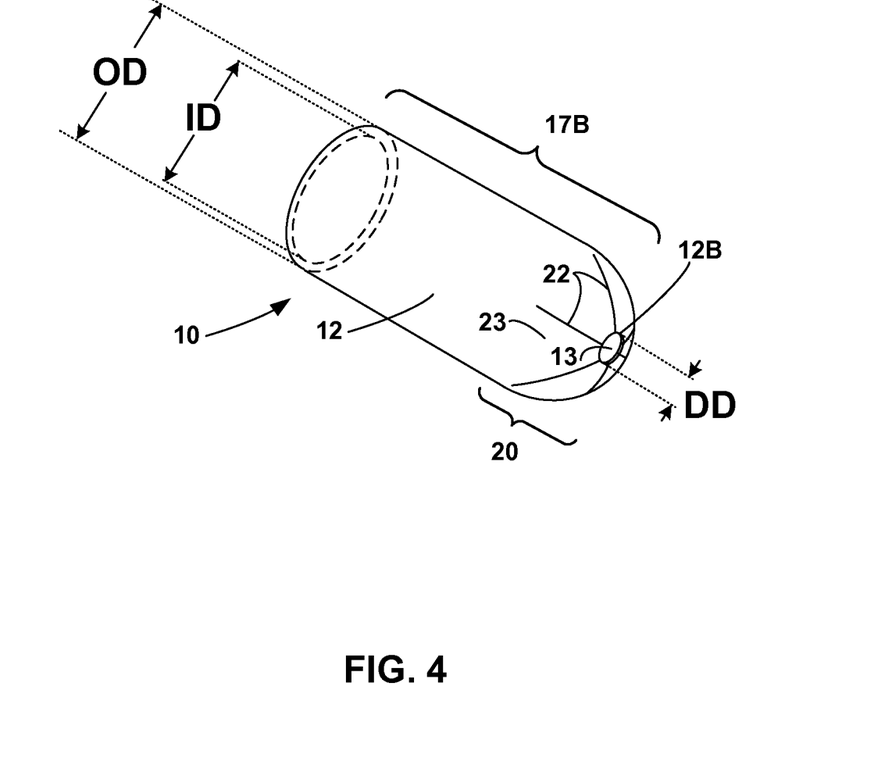
FIG. 4 is a conceptual perspective view of a distal portion of an example elongated body.

FIG. 4 is a conceptual perspective view of distal portion 17B of elongated body 12 that provides another view of taper section 20. As shown, taper section 20 of distal portion 17B defines a taper from the outer body wall of elongated body 12 to distal aperture 13. In some examples, the taper may be described as a convex surface that curves from the OD of the outer body wall to the diameter DD of distal aperture 13 at the distal end 12B of elongated body 12.

In some examples, taper section 20 may be made of semi-flexible material, such that tip flaps 23 remain sufficiently rigid to keep the distal end 12B of elongated body 12 substantially centered on guide member 18 during advancement of distal end 12B through the vasculature of a patient, while also allowing taper section 20 to expand during the deployment of a treatment device distally through distal end 12B.

Additionally or alternatively, tip flaps 23 of taper section 20 may be proximally retractable, allowing tip flaps 23 to be withdrawn into inner lumen 26 and thereby expanding the diameter of distal aperture 13 (DD). For example, some or all of tip flaps 23 may be scored or exhibit a reduced wall thickness at their proximal ends where they join the main body of the distal portion 17B, so that upon application of sufficient pressure in the proximal direction tip flaps 23 can retract into inner lumen 26, creating a larger distal aperture 13 and permitting relatively large thrombi or other material to enter proximally into inner lumen 26.

While it may be desirable in some cases to provide elongated body 12 with a relatively flexible distal portion 17B, increasing the stiffness or hardness of distal portion 17B, including taper section 20, relative to proximal section 17A may provide certain advantages in some examples. For example, increasing the stiffness or hardness of the distal portion 17B may configure distal end 12B of elongated body 12 to resist geometric deformation when distal end 12B of elongated body 12 is engaged with guide member 18 and advanced along guide member 18 through a vasculature of a patient as described further below.

In some examples, taper section 20 and distal portion 17B may be comprised of different materials. For example, taper section 20 may be made of a semi-flexible material as described above, while the remainder of distal portion 17B may be made of a harder (e.g., stiffer) material compared to taper section 20. Distal portion 17B that exhibits the increased stiffness may be a relatively small length of elongated body 12 and, therefore, may not affect the overall flexibility of elongated body 12. In some examples, taper section 20 of distal portion 17B may be relatively short in relation to the length of elongated body 12. For example, taper section 20 may have a length (e.g., a length measured along longitudinal axis 16 of elongated body 12) less than about 10 mm, or less than about 8 mm, or less than about 5 mm, or less than about 3 mm, or less than about 2 mm, or less than about 1 mm, or less than about 0.5 mm. In some examples, the length of taper section 20 may be approximately the same as the diameter of elongated body 12.

Example materials for distal portion 17B and/or taper section 20 include, for example, polymers, such as a polyether block amide (e.g., PEBAX®, commercially available from Arkema Group of Colombes, France), an aliphatic polyamide (e.g., Grilamid®, commercially available from EMS-Chemie of Sumter, S.C.), another thermoplastic elastomer or other thermoplastic material, or combinations thereof. In some examples distal portion 17B and/or taper section 20 of elongated body 12 may include a lubricious outer surface, e.g., a lubricious coating. The lubricating coating may be configured to reduce static friction and/or kinetic friction between elongated body 12 and tissue of the patient as elongated body 12 is advanced through the vasculature. The lubricating coating can be, for example, a hydrophilic coating such as Serene™ available from Surmodics, Inc. of Eden Prairie, Minn.

In some examples, taper section 20 and/or distal portion 17B may be formed as a separate component to elongated body 12 and attached (e.g., thermally bonded or adhered) to elongated body during manufacturing. In other examples, taper section 20 and/or distal portion 17B may be formed integrally with proximal portion 17A, for example by extruding these components as a unit and subsequently molding distal portion 17B into its tapered shape.

Figure 5A:
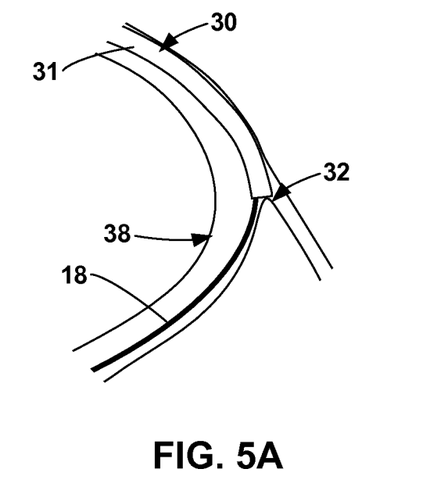
FIG. 5A is a conceptual illustration of a catheter advanced through the vasculature of a patient.

The taper of taper section 20 may help with the navigability of elongated body 12 through the vasculature of a patient. For example, when distal end 12B of elongated body 12 is introduced into vasculature of a patient, distal end 12B of elongated body 12 leads catheter 10 through the vasculature. By tapering the outer diameter of taper section 20 from the outer diameter (OD) of elongated body 12 to the diameter (DD) of distal aperture 13 may reduce the existence of blunt edges, thereby reducing the chance of encountering ledge-effects (e.g., as shown in FIG. 5), or other navigability issues as the clinician advances the catheter 10 through the tight turns of the vasculature of a patient. Additionally or alternatively, in some examples taper section 20 may allow distal end 12B of elongated body 12 to remain substantially centered (e.g., centered or nearly centered) around guide member 18, which may also help with the navigability of elongated body 12.

Figure 5B:
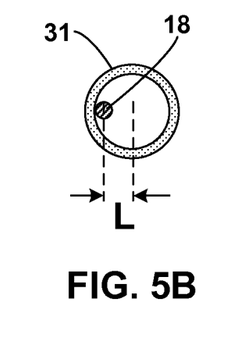
FIG. 5B is a conceptual front-view illustration of a catheter advanced over a guide member.

FIGS. 5A, 5B, 6A, and 6B illustrate how the reduction of a ledge-effect may be obtained from a taper section 20 that is configured to substantially center distal end 12B of catheter 10 relative to guide member 18. FIG. 5A shows elongated body 31 of another example catheter 30 being advanced along guide member 18 through the vasculature 38 of a patient containing a fork or bifurcation on the outside of a curve. Because catheter 30 does not include a taper section 20 at the distal portion, the guide member 18 may contact and ride along the inner wall of elongated body 31, creating a displacement between the center axis of elongated body 31 and the center axis of guide member 18 (e.g., as shown in FIG. 5B, which is a cross-sectional view to the distal end of catheter 30 illustrating the displacement (L) created between the center axis of elongated body 31 and the center axis of guide member 18). As the elongated body 31 of catheter 30 is advanced past a fork and/or a curve in vasculature 38, the displacement (L) between elongated body 31 and guide member 18 causes a portion of elongated body 31 to contact and be resisted by the fork and/or vasculature 38, thus establishing a ledge-effect (e.g., resistance contact area 32 between catheter 30 and vasculature 38 shown in FIG. 5A, and/or abrasion of the vessel wall on the outside of the curve by the outer edge of the distal end of catheter 30).

Figure 6A:
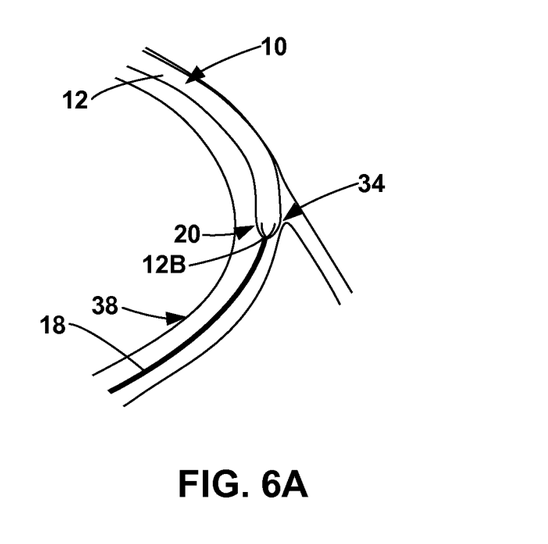
FIG. 6A is a conceptual illustration of a catheter including a taper section advanced through the vasculature of a patient.
Figure 6B:
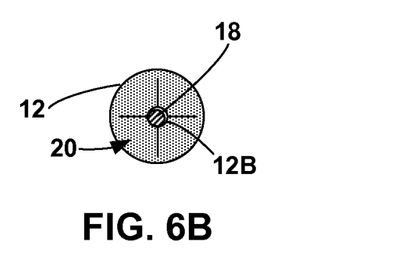
FIG. 6B is a conceptual front-view illustration of a catheter including a taper section advanced over a guide member.

In contrast to catheter 30, catheter 10 includes taper section 20 of distal portion 17B. As shown in FIGS. 6A and 6B, taper section 20 of elongated body 12 helps center the distal end 12B around guide member 18. As a clinician advances elongated body 12 through the vasculature 38 of a patient containing a fork and/or curve, the taper of taper section 20 in conjunction with the self-centering aspect of the distal portion 17B of elongated body 12 around guide member 18 may allow the clinician to more easily advance distal end 12B of catheter 10 past the fork of vasculature 38 with little resistance and reduced ledge-effect (e.g., area 34 shown in FIG. 6A). The centering effect of taper section 20 can be seen in, for example, FIG. 6B, which is a conceptual front-view illustration of catheter 10 showing distal end 12B of elongated body 12 substantially centered about guide member 18.

In some examples, due to the ability of taper section 20 of catheter 10 to self-center relative to a guide member and due to the reduced ledge-effect provided by catheter 10, elongated body 12 of catheter 10 may define a relatively high profile (e.g., larger outer diameters (OD)) without experiencing a significant reduction in navigability. In some examples, catheter 10 defining a relatively high profile may be advanced along guide member 18 through the vasculature of a patient without the assistance of an intermediate device (e.g., a lower profile catheter advanced over guide member 18 and positioned within elongated body 12, to assist with the advancement of the higher profile catheter to the treatment site.).

As shown in FIG. 4, elongated body 12 defines a plurality of slits 22 that are open from distal aperture 13 (e.g., extending from distal aperture 13 along a portion of elongated body 12). In some examples, plurality of slits 22 may extend along the length or short of the length of taper section 20. In other examples, plurality of slits 22 may extend beyond the length of taper section 20 and along part of distal portion 17B.

Figure 7A:
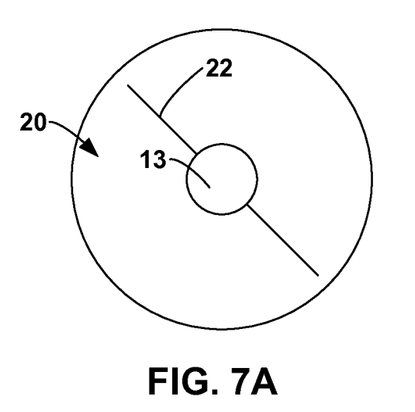
FIGS. 7A-7E are conceptual front-view illustrations of example taper sections of a catheter.
Figure 7B:
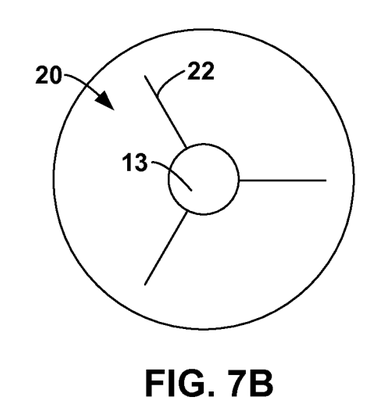
Figure 7C:
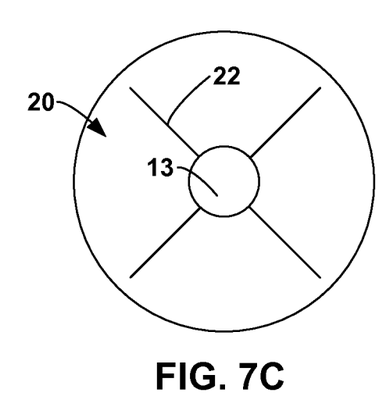
Figure 7D:
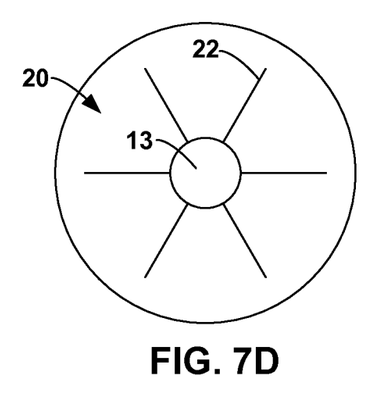
Figure 7E:
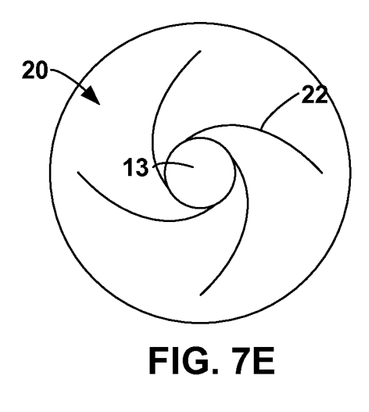

Plurality of slits 22 may take on any shape and may be present in any quantity along distal portion 17B. FIGS. 7A-7E show various examples of a taper section 20 including a distal aperture 13 and plurality of slits 22 having different configurations. For example, FIGS. 7A-7D show a taper section 20 containing two (FIG. 7A), three (FIG. 7B), four (FIG. 7C), and six (FIG. 7D) slits 22, all extending radially outward from the distal aperture 13. FIG. 7E provides an additional and alternative example with taper section 20 containing four slits 22 spiraling radially outward from distal aperture 13. In some examples, having slits 22 spiral radially outward from distal aperture 13 may provide longer and relatively more flexible tip flaps 23 (as compared to those made via straight slits 22) without unduly extending slits 22 proximally along elongated body 12.

In some examples, plurality of slits 22 may be formed by etching, cutting, or molding slits 22 into distal portion 17B after constructing taper section 20. This may be performed using a variety of techniques including, for example, die cutting, laser cutting, chemical etching, or any other suitable technique.

Plurality of slits 22 may help with the advancement of catheter 10 through the vasculature of a patient as well as with the performance of various medical procedures. For example, plurality of slits 22 may allow distal portion 17B to define a relatively small distal opening (e.g., distal aperture 13 defined by diameter DD) that engages with guide member 18 while a clinician advances distal portion 17B through the vasculature of the patient, thereby reducing potential navigability issues (e.g., ledge-effects). Additionally, plurality of slits 22 may allow the distal opening of catheter 10 to expand to a relatively large effective distal opening (e.g., the size of inner diameter ID) by, for example, retracting tip flaps 23 into inner lumen 26 or straightening taper section 20 such that tip flaps 23 extend distally parallel to longitudinal axis 24. The relatively large effective distal opening may assist the clinician perform various medical procedures such as the aspiration of a thrombosis, the deployment of a treatment device (e.g., a thrombectomy device, stent, coil, filter), or the like, which may be more easily performed as a result of the relatively larger distal opening established by plurality of slits 22.

Figure 8:
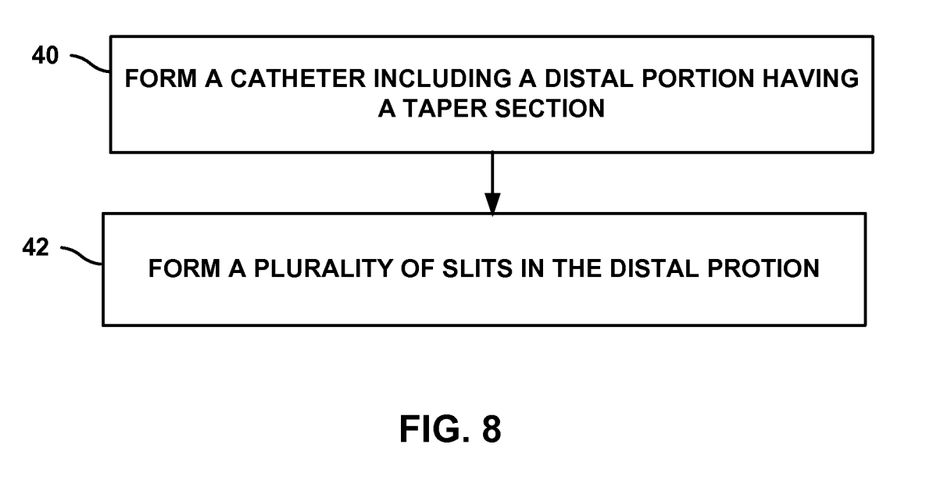
FIG. 8 is a flow diagram of an example method of forming the catheter of FIG. 1.

Catheter 10 described herein may be formed using any suitable technique. FIG. 8 is a flow diagram of example method of forming catheter 10. The technique of FIG. 8 is described with reference to FIGS. 1-3 for illustrative purposes, however, such descriptions are not intended to be limiting and the techniques of FIG. 8 may be used to form other catheters or the catheter of FIGS. 1-3 may be formed using other techniques.

In accordance with the technique shown in FIG. 8, catheter 10 may be formed (40) to include elongated body 12 extending between proximal end 12A and distal end 12B having distal aperture 13 at distal end 12B. Elongated body 12 may define inner lumen 26 and include an outer body wall (e.g. a sidewall of elongated body 12) having a wall cross-sectional diameter (e.g., the cross-sectional diameter (OD) of the sidewall of elongated body 12). Forming catheter 10 (40) may include forming distal portion 17B of elongated body 12 that includes taper section 20 tapering from the outer body wall (e.g., the sidewall of elongated body 12) to distal aperture 13. In some examples, the diameter of distal aperture 13 may be formed such that it an aperture diameter (DD) greater than zero and less than the wall cross-sectional diameter (e.g., OD). As described above, in some examples the diameter of distal aperture 12 may be sized such that is substantially equal (e.g., equal or nearly equal) to the diameter of guide member 18.

In some examples, in the technique shown in FIG. 8, an inner liner may be positioned over a mandrel that defines a tapered end corresponding to the configuration of taper section 20. The inner liner may be heat shrunk or stretched onto the mandrel in order to conform the inner surface of the inner liner to the outer surface of mandrel and acquire the tapered profile of the mandrel. A structural support member, such as a coil member and/or a braided member, may be positioned over the inner liner, and then an outer jacket may be positioned over the structural support member. In some examples, the structural support member is not present in taper section 20. The outer jacket can, for example, be heat shrunk over the structural support member and the inner liner.

The technique of FIG. 8 also may include forming plurality of slits 22 in distal portion 17B of the elongated body 12 (42). Plurality of slits 22 may be formed (42) such that the slits open to distal aperture 13 (e.g., extend radially or spirally radially outward from distal aperture 13). The plurality of slits may define a plurality of tip flaps 23 along taper section 20 of distal portion 17B. In some examples, as described above, plurality of slits 22 may extend the length of taper section 20, fall short of the length of taper section 20, or extend beyond the length of taper section 20 into part of distal portion 17B.

As described above, in some examples tip flaps 23 defined by plurality of slits 22 may be configured to retract proximally along distal portion 17B (e.g., into inner lumen 26) to change the size of distal aperture 13 to, for example, introduce a treatment device into the vasculature of a patient.

Figure 9:
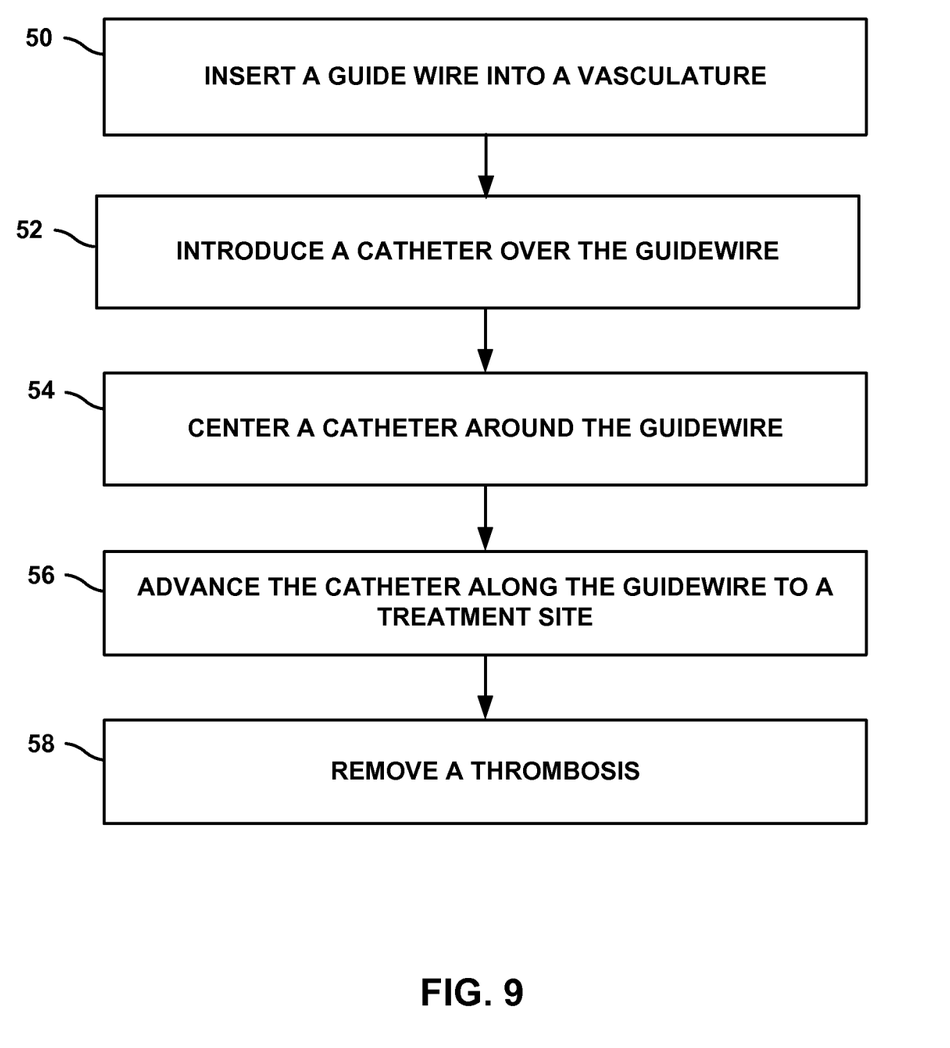
FIG. 9 is a flow diagram of an example method of using the catheter of FIG. 1.

FIG. 9 is a flow diagram of an example method of using catheter 10. Similarly the technique of FIG. 9 is described with reference to FIGS. 1-3 for illustrative purposes, however, such descriptions are not intended to be limiting and the techniques of FIG. 9 may be used with other catheters or the catheter of FIGS. 1-3 may be used for other applications.

In some examples, a method of using catheter 10 comprises introducing guide member 18 into a vasculature (e.g., an intracranial blood vessel) of a patient via an access point (e.g., a femoral artery) (50) and introducing catheter 10 (e.g., distal portion 17B of elongated body 12) over guide member 18 (52). Catheter 10 may include taper section 20 configured to resist geometric deformation, even as it engages with guide member 18, thereby allowing distal end 12B to remain substantially centered around guide member 18 (54). For example, when introducing guide member 18 into the vasculature of a patient, a curve may be formed in guide member 18. Distal portion 17B of elongated body 12 may be advanced over the curve in the guide member and taper section 20 of catheter 10 may resist geometric deformation and remain substantially centered around guide member 18 when the catheter is advanced over the curve to a greater degree than would occur in the absence of taper section 20. Taper section 20 (and its effect of centering distal portion 17B of elongated body 12 around guide member 18 (54)) may therefore inhibit distal portion 17B from damaging an inner wall of the vasculature.

The technique of FIG. 9 also may include advancing distal portion 17B of catheter 10 along guide member 18 (e.g., over guide member 18) to a treatment site within the vasculature of a patient (56). Once distal portion 17B of elongated body 12 is positioned at the target tissue site, which may be proximal to thromboembolic material (e.g., a thrombus), the thromboembolic material be removed from the vasculature via distal aperture 13 and inner lumen 26 of elongated body 12 (58). For example, the thromboembolic material may be aspirated from the vasculature by at least a vacuum force to inner lumen 26 of elongated body 12 via hub 14, which may cause the thromboembolic material to be introduced into inner lumen 26 via distal aperture 13 (58). As another example, the thromboembolic material may be removed from the vasculature using another technique, such as via a retrieval device (58). The thromboembolic material may be located using any suitable technique, such as intravascular ultrasound or carotid Doppler imaging techniques.

Various examples have been described. These and other examples are within the scope of the following claims.

What is claimed is:

1. A catheter comprising:
   an elongated body extending between a proximal end and a distal end, and defining an inner lumen, an outer body wall having a wall cross-sectional diameter, and a distal aperture at the distal end,
   wherein a distal portion of the elongated body comprises a taper section that tapers from the outer body wall of the distal portion to the distal aperture, wherein the taper section comprises a plurality of tip flaps defined by a plurality of slits open to the distal aperture, wherein at least some of the tip flaps of the plurality of tip flaps comprise at least one of a scored segment or a reduced wall thickness at a proximal end of the respective tip flap where the tip flap joins with the outer body wall, wherein the reduced wall thickness is measured relative to thicknesses of adjacent portions of the respective tip flap and the outer body wall, and wherein the at least one of the scored segment or the reduced wall thickness is configured so that upon application of pressure on the plurality of tip flaps in the proximal direction, the plurality of tip flaps fold at the at least one of the scored segment or the reduced wall thickness and withdraw proximally into the inner lumen to expand an effective diameter of the distal aperture,
   wherein the effective diameter of the distal aperture is greater than zero and less than the wall cross-sectional diameter, wherein the distal portion defining the plurality of slits is configured to substantially center the distal end around a guide member when the guide member is introduced in the inner lumen and extends through the distal aperture.

2. The catheter of claim 1, wherein the plurality of slits extend radially outward from the distal aperture.

3. The catheter of claim 1, wherein the plurality of slits spiral radially outward from the distal aperture.

4. The catheter of claim 1, wherein the effective diameter of the distal aperture is about 0.2 mm to about 0.8 mm before the expansion of the effective diameter.

5. The catheter of claim 4, wherein the effective diameter of the distal aperture is about 0.36 mm before the expansion of the effective diameter.

6. The catheter of claim 1, wherein the taper section comprises a lubricious outer surface.

7. The catheter of claim 1, wherein the distal portion is thermally bonded to a proximal portion of the elongated body.

8. The catheter of claim 1, wherein the taper section has a total length of less than about 10 mm.

9. The catheter of claim 1, wherein the outer body wall lacks any openings therein.

10. The catheter of claim 9, wherein the outer body wall is a sidewall of the elongated body.

11. The catheter of claim 1, wherein the distal aperture is positioned in a distalmost tip of the catheter.

12. The catheter of claim 1, wherein the elongated body defines a sidewall thickness measured from an outer surface of the catheter to an inner surface that defines the inner lumen, wherein the sidewall thickness of the elongated body is reduced where the tip flap joins with the outer body wall to form the reduced wall thickness.

13. The catheter of claim 1, wherein at least some of the tip flaps of the plurality of tip flaps comprise the scored segment at the proximal end of the respective tip flap where the tip flap joins with the outer body wall.

14. An assembly comprising:
    a catheter comprising an elongated body extending between a proximal end and a distal end, and defining an inner lumen, an outer body wall having a wall cross-sectional diameter, and a distal aperture at the distal end, wherein a distal portion of the elongated body comprises a taper section that tapers from the outer body wall to the distal aperture, the taper section comprising a plurality of tip flaps defined by a plurality of slits open to the distal aperture, wherein the distal aperture has an aperture diameter greater than zero and less than the wall cross-sectional diameter, wherein at least some of the tip flaps of the plurality of tip flaps comprise at least one of a scored segment or a reduced wall thickness at a proximal end of the respective tip flap where the tip flap joins with the outer body wall, wherein the reduced wall thickness is measured relative to thicknesses of adjacent portions of the respective tip flap and the outer body wall, and wherein the at least one of the scored segment or the reduced wall thickness is configured so that upon application of pressure on the plurality of tip flaps in the proximal direction, the plurality of tip flaps at the at least one of the scored segment or the reduced wall thickness and withdraw proximally into the inner lumen to expand an effective diameter of the distal aperture; and
    a guide member disposed within the inner lumen of the catheter and extending through the distal aperture of the catheter, wherein the distal end of the elongated body engages with the guide member to substantially center the distal end of the of the elongated body relative to the guide member.

15. The assembly of claim 14, wherein the plurality of slits extend radially outward from the distal aperture.

16. The assembly of claim 14, wherein the plurality of slits spiral radially outward from the distal aperture.

17. The assembly of claim 14, wherein the aperture diameter of the distal aperture is about 0.2 mm to about 0.8 mm before the expansion of the aperture diameter.

18. The assembly of claim 14, wherein the aperture diameter of the distal aperture is about 0.36 mm before the expansion of the aperture diameter.

19. The assembly of claim 14, wherein the taper section of the catheter comprises a lubricious outer surface.

20. The assembly of claim 14, wherein the taper section has a total length of less than about 10 mm.

21. The assembly of claim 14, wherein the outer body wall lacks any openings therein.

22. The assembly of claim 21, wherein the outer body wall is a sidewall of the elongated body.

23. The assembly of claim 14, wherein the distal aperture is positioned in a distalmost tip of the catheter.

24. The assembly of claim 14, wherein the guide member comprises a guidewire.

25. The assembly of claim 14, wherein the catheter comprises a first catheter, and wherein the guide member comprises a second catheter.

* * * * *